(12) United States Patent
Shen et al.

(10) Patent No.: US 9,445,718 B2
(45) Date of Patent: Sep. 20, 2016

(54) OPTICAL SYSTEM AND MEASUREMENT METHOD THEREOF

(71) Applicants: Tsu-Wang Shen, Hualien (TW);
Tsung-Yu Ho, Taipei (TW);
Weng-Kong Tam, Hualien (TW);
Yu-Nong Wang, New Taipei (TW)

(72) Inventors: Tsu-Wang Shen, Hualien (TW);
Tsung-Yu Ho, Taipei (TW);
Weng-Kong Tam, Hualien (TW);
Yu-Nong Wang, New Taipei (TW)

(*) Notice: Subject to any disclaimer, the term of this patent is extended or adjusted under 35 U.S.C. 154(b) by 175 days.

(21) Appl. No.: 14/255,111

(22) Filed: Apr. 17, 2014

(65) Prior Publication Data

US 2014/0313483 A1 Oct. 23, 2014

Related U.S. Application Data

(60) Provisional application No. 61/812,865, filed on Apr. 17, 2013.

(51) Int. Cl.
*A61B 3/14* (2006.01)
*A61B 3/15* (2006.01)

(52) U.S. Cl.
CPC .................... *A61B 3/154* (2013.01)

(58) Field of Classification Search
CPC ...... A61B 3/152; A61B 3/145; A61B 3/103; A61B 3/1015; A61B 3/14; A61B 3/12
USPC .................... 351/205, 206, 208, 246
See application file for complete search history.

(56) References Cited

U.S. PATENT DOCUMENTS

| | | | | |
|---|---|---|---|---|
| 4,861,155 A | * | 8/1989 | Downey | 351/212 |
| 6,474,815 B1 | * | 11/2002 | Ulbers et al. | 351/214 |
| 2002/0018179 A1 | * | 2/2002 | Hayashi et al. | 351/204 |

* cited by examiner

*Primary Examiner* — James Greece
(74) *Attorney, Agent, or Firm* — Chun-Ming Shih; HDLS IPR Services

(57) ABSTRACT

An optical system for measuring an observed object includes an illuminant component, an imaging component, and an optical component. The illuminant component generates a measuring light. The optical component including a mirror and a beam splitter is located between the illuminant component and the imaging component. The mirror is located between the illuminant component and the observed object, the beam splitter is located between the mirror, the observed object, and the imaging component. The measuring light is projected to the observed object via the mirror and beam splitter, and an imaging light that has been generated from the illuminant component and reflected by the observed object is projected to the imaging component via the beam splitter, the imaging light and the measuring light intersect at the beam splitter. The present invention also provides a measurement method.

16 Claims, 6 Drawing Sheets

OPTICAL SYSTEM AND MEASUREMENT METHOD THEREOF

CROSS REFERENCE TO RELAYED APPLICATIONS

This application claims priority of U.S. Provisional Application No. 61/812,865 filed on Apr. 17, 2013 under 35 U.S.C. §119(e), the entire contents of which are hereby incorporated by reference.

BACKGROUND OF THE INVENTION

1. Field of the Invention

The present invention relates to an optical system and a measurement method, and in particular to an optical system for measurement and measurement method for measuring curvature and pressure of a surface.

2. Description of Related Art

In general, the modem microscope optical system, such as slit lamp or optical coherence tomography (OCT) measuring instrument require observed object (such as patient's eye) to stay on a position with fixed focal point from a light generator. For example, a slit lamp (or OCT measuring instrument) require patient's chin be placed on a supporting frame, and forehead is in contact with a blocking frame of the optical system to obtain a measurement result. The fixed distance between the supporting frame (or the blocking frame) and light generator provides the optical system a clear observation and sharp light marker on the patient's eye.

Meanwhile, inspector is also required to stay on another position with predetermined distance from the supporting frame, or a misjudge measurement will be occurred by unclear observation.

The light generator generates a linear light with high intensity and is applied to partially light the observed object, so that inspector can observe the observed object and determined conditions of the observed object.

If the observed object is out of focus, this can cause a burr marker and substantially any distance measurement can be misjudged.

The fixed distance between the light generator and observed object and the predetermined distance between the observed object and inspector make a sharp light generated from the light generator to light the observed object, and inspector can view a clear observation. However, the supporting frame for fixing the observed object at the fixed point from the light generator and inspector makes the optical system very bulky and not easy to carry for using outside a clinic, such as homecare or other out-patient care.

SUMMARY OF THE INVENTION

The object of the present invention is to provide an optical system, the optical system projects a measuring light to an observed object and transmits an imaging light that has been projected to the observed object and reflected thereby to a display for convenient inspection. Besides, the optical system has advantage of compactness.

Accordingly, the optical system for measuring an observed object comprises an optical apparatus. The optical apparatus comprises and illuminant component, an imaging component, and an optical component. The illuminant component generates a measuring light. The optical component is located between the illuminant component and the imaging component. The optical component comprises a mirror and a beam splitter. The mirror is located between the illuminant component and the observed object, and the beam splitter is located between the mirror, the observed object, and the imaging component.

The measuring light is projected to the observed object via the mirror and the beam splitter, an imaging light that has been generated from the illuminant component and reflected by the observed object is projected to the imaging component via the beam splitter, the imaging light and the measuring light intersecting at the beam splitter.

Thereby the volume of the optical system having function of inspection can be effectively reduced for easily carrying, using out of clinic or homecare or other out-patient care.

In an embodiment of the present invention, the illuminant component comprises a lighting module and a lighting lens assembly. The lighting module comprises a light emitter and a light pattern conditioner. The light emitter is light emitting diode, which has advantage of compact, well luminous efficacy, and long lifetime. The light pattern conditioner receives the measuring light emitted from the light emitter and optically modifies the measuring light to have a predetermined pattern. The light pattern conditioner is, for example, aperture stop. The lighting lens assembly converges the measuring light passing through the light pattern conditioner on the mirror to reduce divergent angle of the measuring light.

The imaging component comprises an ocular assembly and an objective assembly, the objective assembly is adjacent to the beam splitter, and the ocular assembly is far away from the beam splitter. The objective assembly and the ocular assembly collectively modify magnification of an observed image with imaging light. The imaging system further comprises a reflecting component arranged between the ocular assembly and the objective assembly for adjusts optical path of the observed image with imaging light passing through the objective assembly and projected to the ocular assembly.

The optical system further comprises a light receiver and an electronic component. The light receiver is adjacent to the ocular assembly and configured to receive the observed image with imaging light and convert the observed image with imaging light into corresponding electric signal. The electronic component comprising a display is configured to receive the electric signal.

In another embodiment of the present invention, the optical system further comprises a fastening component. The fastening component comprises a first end and a second end opposite to the first end. The fastening component also forms a first through-hole, a second through-hole, and an opening. The first through-hole is parallel to the second through-hole; the first through-hole and the second through-hole extend from the first end to the second end; the opening communicates with the second through-hole.

The illuminant component is arranged within the second through-hole and the lighting module is placed on the first end, the imaging component is arranged within the first through-hole and the ocular assembly is placed on the first end. The optical component is connected to the second end; the mirror corresponds to the second through-hole, and the beam splitter corresponds to the first through-hole.

In order to provide index effect, the optical component further comprises a plurality of indicators arranged at one side of the beam splitter and the mirror and opposite to the imaging component.

The optical system further comprises a contacting component arranged between the optical component and the observed object, and connected to the optical component and opposite to the imaging component.

In order to modify magnification, the optical system comprises a synchronal-movable mount holding the lighting lens assembly and the objective assembly. The synchronal-movable mount makes the lighting lens assembly and the objective assembly move backward and forward within the second through-hole and the first through-hole.

In the other embodiment of the present invention, the optical system further comprises another optical apparatus, an included angle is formed between the optical apparatuses, the optical apparatuses respectively project a measuring light to the observed object, and the measuring lights intersect at the observed object, thereby a stereoscopic image is then generated.

The optical system also comprises two light receivers and an electronic component. The light receivers correspond to the ocular assemblies of the imaging components of the optical apparatuses. Each light receiver is configured to receive imaging light been generated from the illuminant component and reflected by the observed object, and converts the observed image with imaging light into corresponding electric signals. The electronic component comprises a display is configured to receive the electric signals via wire transmission or wireless transmission.

The optical system further comprises a microscopy module and an adjusting component, the microscopy module is arranged between the optical component and the observed object and connected to the optical component. The adjusting component connected to the beam splitter for adjusting arrangement angle thereof, thereby the transmitting angle of the measuring light and the observed image with imaging light can be effectively controlled.

In a further embodiment of the present invention, a measurement method applied to the optical system mentioned above is provided. The measurement method is used for measuring an eyeball, the measurement method comprises following steps: (a) projecting a measuring light to the eyeball; (b) receiving an imaging light reflected by the eyeball; (c) measuring a first distance between a surface of the eyeball and the optical system; (d) measuring a second distance between an extending line of a center of the eyeball and rim of the objective assembly; (e) measuring a third distance between an edge of the imaging light and the center; (f) calculating a ratio of the third distance to the second distance; (g) calculating a radius of the eyeball, wherein a ratio of the radius to a sum of the radius and the first distance is equal to the ratio of the third distance to the second distance; (h) calculating an angle included between the center to the edge of the imaging light, wherein the angle has arctangent equal to a ratio of the third distance to the radius; and (i) calculating a first surface curvature of the surface, wherein the first surface curvature is inverse to a ratio of the angle to the third distance.

In another embodiment of the present invention, the optical measuring method further comprises following steps: (j) repeating step (a) to (i), and obtaining a second surface curvature; and (k) calculating a difference between the first surface curvature and the second surface curvature to obtain a pressure of the eyeball.

BRIEF DESCRIPTION OF DRAWING

The features of the invention believed to be novel are set forth with particularity in the appended claims. The invention itself, however, may be best understood by reference to the following detailed description of the invention, which describes an exemplary embodiment of the invention, taken in conjunction with the accompanying drawings, in which:

DETAILED DESCRIPTION OF THE INVENTION

Figure 1:
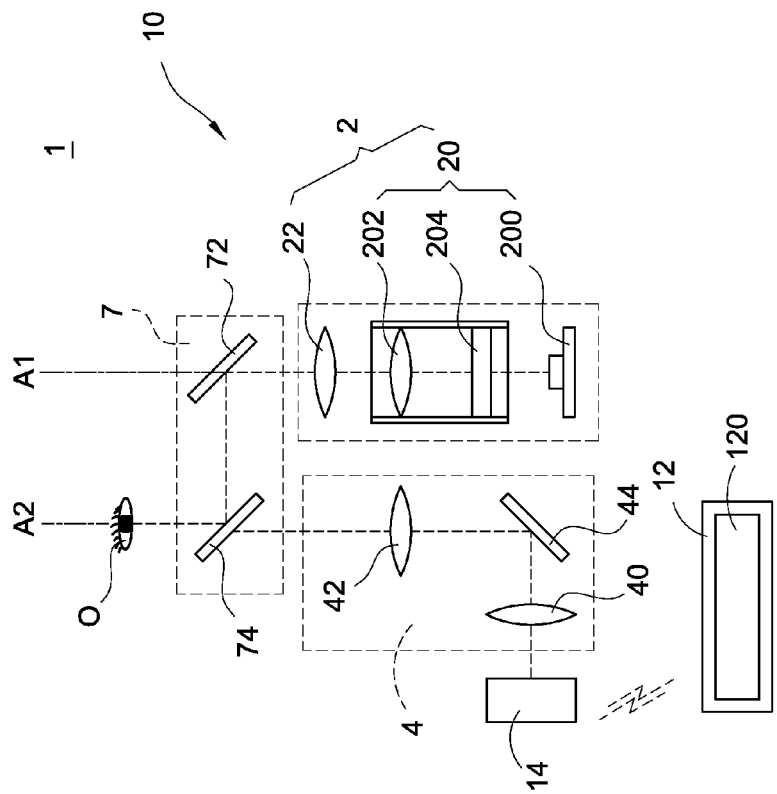
FIG. 1 is a schematic view of an optical system according to a first embodiment of the present invention.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and components are schematically shown in order to simplify the drawing.

Reference is made to FIG. 1, which is a schematic view of an optical system according to a first embodiment of the present invention. The optical system 1 includes an optical apparatus 10. The optical apparatus 10 includes an illuminant component 2, an imaging component 4, and an optical component 7. The illuminant component 2 generates a measuring light with uniform intensity. The measuring light is projected to an observed object O via the optical component 7 located between the illuminant component 2 and the imaging component 7 so that the observed object O is lit. An imaging light that has been generated from the illuminant component 2 and reflected by the observed object O is projected to the imaging component 4 through the optical component 7 so that an inspector can inspect the observed object O via the imaging component 4.

The optical system 1 also includes a computing component 12 and a light receiver 14. The light receiver 14 receives the observed image with imaging light passing through the imaging component 4 and converts the observed image with imaging light into corresponding electric signal by photoelectric conversion, and then transmits the electric signal to the computing component 12. The electric signal transmitted between the light receiver 14 and the computing component 12 can be wire transmission or wireless transmission. The computing component 12 includes a display 120 for showing objective images corresponding to electric signals so that inspector can inspect the objective images of the observed object O. The display 120 is electrically connected to the computing component 12 via wire connection or wireless connection, however, the display 120 can be assembled with the computing component 12. The computing component 12 is configured to analyze and process the objective images.

In this embodiment, the observed object O is, for example, eyeball, the measuring light has a predetermined patter such as linear, cross-shaped or circular. The pattern of the measuring light can be modified according the observed object O for providing proper illuminated effect.

The illuminant component 2 includes a lighting module 20 for generating the measuring light with predetermined pattern. The lighting module 20 includes a light emitter 200, a converging lens assembly 202, and a light pattern conditioner 204. The light emitter 200 emits the measuring light, and in this embodiment, the light emitter 200 is, for example, light emitting diode (LED). The LED has advantages of compact, well luminous efficacy, and long lifetime. The volume of the optical system 1 using LED can be reduced. The well luminous efficacy means that most electric power entering the LED is converted into light, and only small section of electric power entering the LED is converted into heat. Comparing to the conventional optical system using incandescent lamp for generating measuring light, the heat generated by the optical system 1 is reduced and increase safety. Moreover, the lifetime of LED is longer than that of incandescent lamp, which substantially reduces probability of replacement. Furthermore, light emitted from the LED can be limited to a particular wavelength, so that in assemble the optical system 1, the LED is choose for emitting light with particular wavelength according to application field. Comparing to conventional optical system, the optical system 1 omits a filter arranged in front of the incandescent lamp for filtering unnecessary wavelength of light.

The light pattern conditioner 204 receives the measuring light emitted from the light emitter 200 and modified light amount passing therethrough to form the particular pattern. The light pattern conditioner 204 is, for example, aperture stop. The pattern of the measuring light passing through the light pattern conditioner 204 can be linear, cross-shaped, or circular. The light pattern conditioner 204 may also limit the size of light point projected to the observed object O, in the other words, the light pattern conditioner 204 limits lighting area of the observed object O where the measuring light is projected.

The converging lens assembly 202 includes one or more convex lenses, however, the converging lens assembly 202 may also include concave lenses. The converging lens assembly 202 converges the measuring light on the optical component 7.

The illuminant component 2 further includes a lighting lens assembly 22 arranged between the converging lens assembly 202 and the optical component 7 for collimating the measuring light to the optical component 7. In the other words, the lighting lens assembly 22 limits the divergent angle of the measuring light to increase light usage efficiency.

The optical component 7 includes a mirror 72 and a beam splitter 74. The mirror 72 is located between the illuminant component 2 and the observed object O and adjacent to the illuminant component 2, and the beam splitter 74 is adjacent to the mirror 72 and is disposed between the observed object O and the imaging component 4. The splitter 74 is adjacent to the imaging component 4 for adjusting optical path of the measuring light so that the measuring light can be projected to the observed object O.

The measuring light emitted from the light emitted 200 passes through the light pattern conditioner 204, the converging lens assembly 202, the lighting lens assembly 22 aligned in a first axis A1 and transmits to the mirror 72. The mirror 72 is also aligned in the first axis A1. The mirror 72 reflects the measuring light such that the optical path of the measuring light is bent and substantially perpendicular to the first axis A1. The measuring light reflected by the mirror 72 is then projected to the observed object O via the beam splitter 74.

The imaging component 4 includes an ocular assembly 40 and an objective assembly 42. The ocular assembly 40 and the objectively assembly 42 are respectively includes at least one lens. The objective assembly 42 is adjacent to the observed object O (or the beam splitter 74), and the ocular assembly 40 is far away from the observed object O (or the beam splitter 74). The imaging component 4 may further include a reflecting component 44 arranged between the ocular assembly 40 and the objective assembly 42 for adjusting optical path of the observed image with imaging light.

The imaging light that has been generated from the illuminant component 2 and reflected by the observed object O passes through the light splitter 72, the objective assembly 42 aligned in a second axis A2 and transmits to the reflecting component 44. The reflecting component 44 is also aligned in the second axis A2. The imaging light and the measuring light intersect at the beam splitter 74. The reflecting component 44 reflects the observed image with imaging light and bent the optical path thereof such that the observed image with imaging light can be projected to the ocular assembly 40. The second axis A2 is parallel to the first axis A1.

The light receiver 14 is adjacent to the ocular assembly 40. The light receiver is configured to receive the observed image with imaging light passing through the ocular assembly 40 and convert the observed image with imaging light into corresponding electric signal by photoelectric conversion. The light receiver 14 transmits the electric signal to the computing component 12 thereafter by wire transmission or wireless transmission. Therefore the inspector can inspect objective images of the observed object O.

Figure 2:
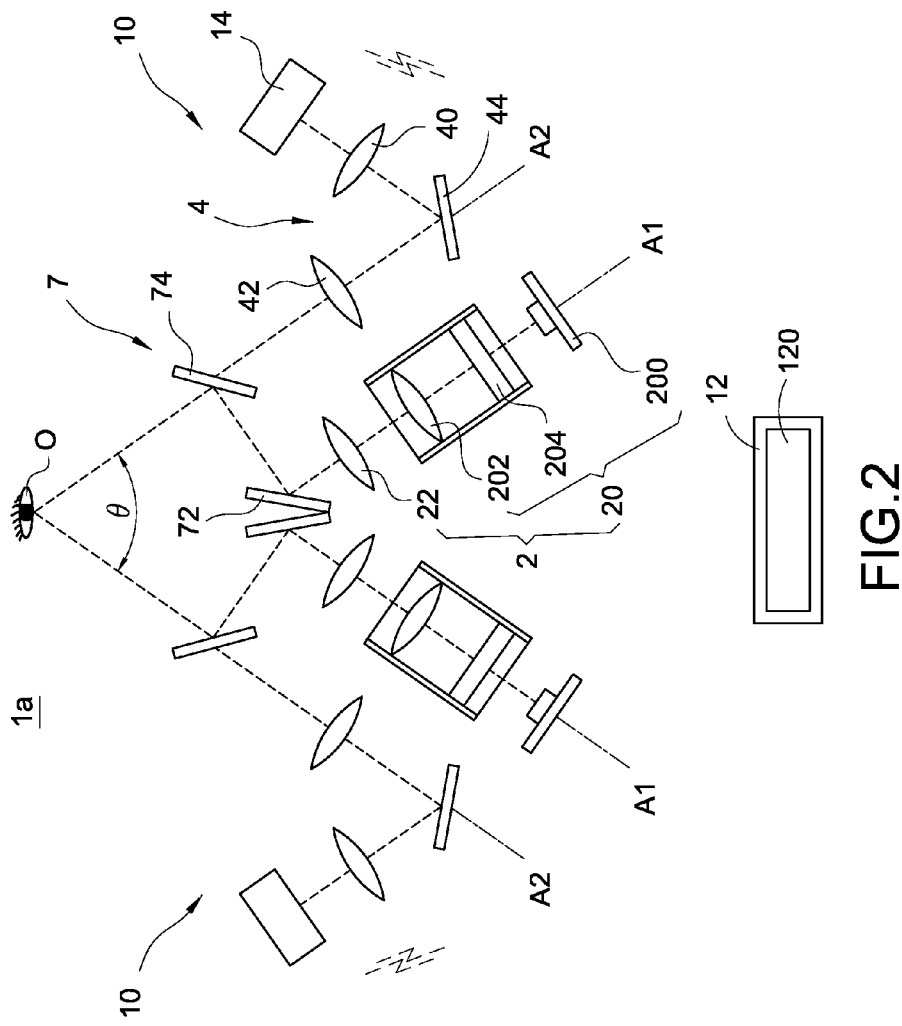
FIG. 2 is a schematic view of an optical system according to a second embodiment of the present invention.

Referred is made to FIG. 2, which is a schematic view of an optical system according to a second embodiment of the present invention. The optical system 1a shown in FIG. 1 is similar to the optical system 1 shown in FIG. 1 mentioned above, and the same reference numbers are used in the drawings and the description to refer to the same parts. It should be noted that the optical system 1a includes two optical apparatuses 10, and an included angle θ is formed between the optical apparatuses 10. The included angle θ is an acute angle.

Each optical apparatus 10 generates a measuring light to project the observed object O, and the measuring lights intersect at the observed object O. Each measuring light emitted from the light emitted 200 and passing through the light pattern conditioner, the converging lens assembly 200 aligned in the first axis A1 is transmitted to the mirror 72. The mirror 72 is also aligned in the first axis A1. The measuring light reflected by the mirror 72 is then transmitted to the light splitter 72 aligned in the second axis A3 and projected to the observed object O. The second axis A2 is parallel to the first axis A1.

The imaging light that has been generated from the illuminant component 2 and reflected by the observed object O passes through the light splitter 72, the objective assembly 42 aligned in the second axis A2 and transmits to the reflecting component 44. The reflecting component 44 is also aligned in the second axis A2. The imaging light and the measuring light intersect at the beam splitter 74. The reflecting component 44 reflects the observed image with imaging light and bent the optical path thereof such that the observed image with imaging light can be projected to the ocular assembly 40. The second axis A2 is parallel to the first axis A1. The light receiver 14 arranged behind the ocular assembly 40 receives the observed image with imaging light passing through the ocular assembly 40 and converts the observed image with imaging light into corresponding electric signal by photoelectric conversion. The light receiver 14 transmits the electric signal to the computing component 12 thereafter by wire transmission or wireless transmission. Therefore inspector can inspect objective image corresponds to the observed object O via the display 120 electrically connected to the computing component 12.

In this embodiment, the second axes A2 of the optical apparatuses intersect at the observed object O. In the other words, the optical apparatuses 10 illuminant the observed object O in different angles, and the light receivers 14 respectively receives observed images with the imaging lights that has been generated from the illuminant components 2 and reflected by illuminated observed object O. The light receivers 14 respectively converts the observed images with the imaging lights into corresponding electric signal by photoelectric conversion and transmits the electric signals to the computing component 12. The computing component 12 computes the electric signals and shows a stereoscopic image corresponding to the computed electric signal. Therefore, inspector can inspect the stereoscopic image of the observed object O. The function and relative description of other components of the optical system 1a are the same as that of first embodiment mentioned above and therefore the descriptions are not repeated here for brevity, and the optical system 1a can achieve the functions as the optical system 1 does.

Figure 3:
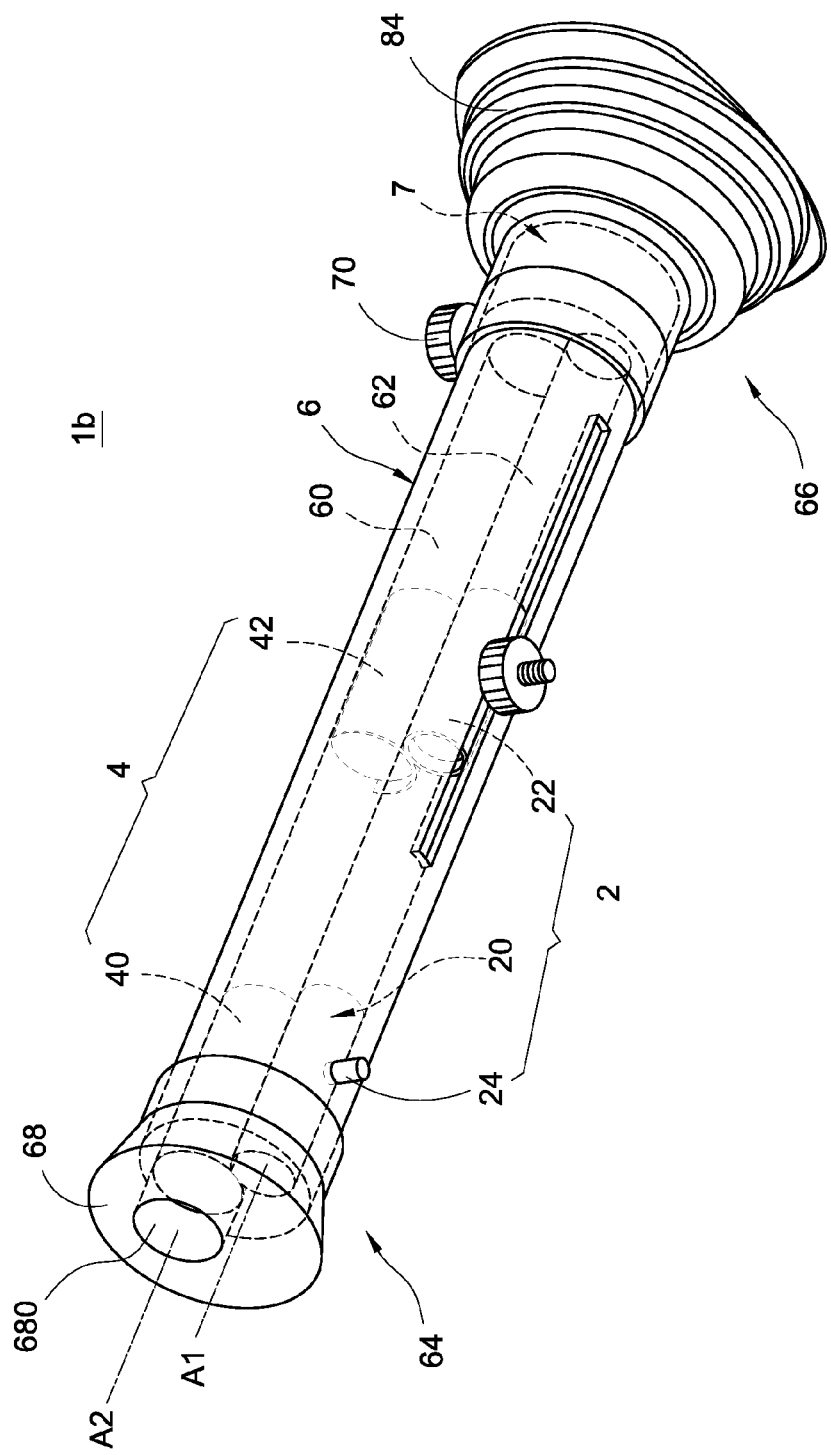
FIG. 3 is a perspective view of an optical system according to a third embodiment of the present invention.
Figure 4:
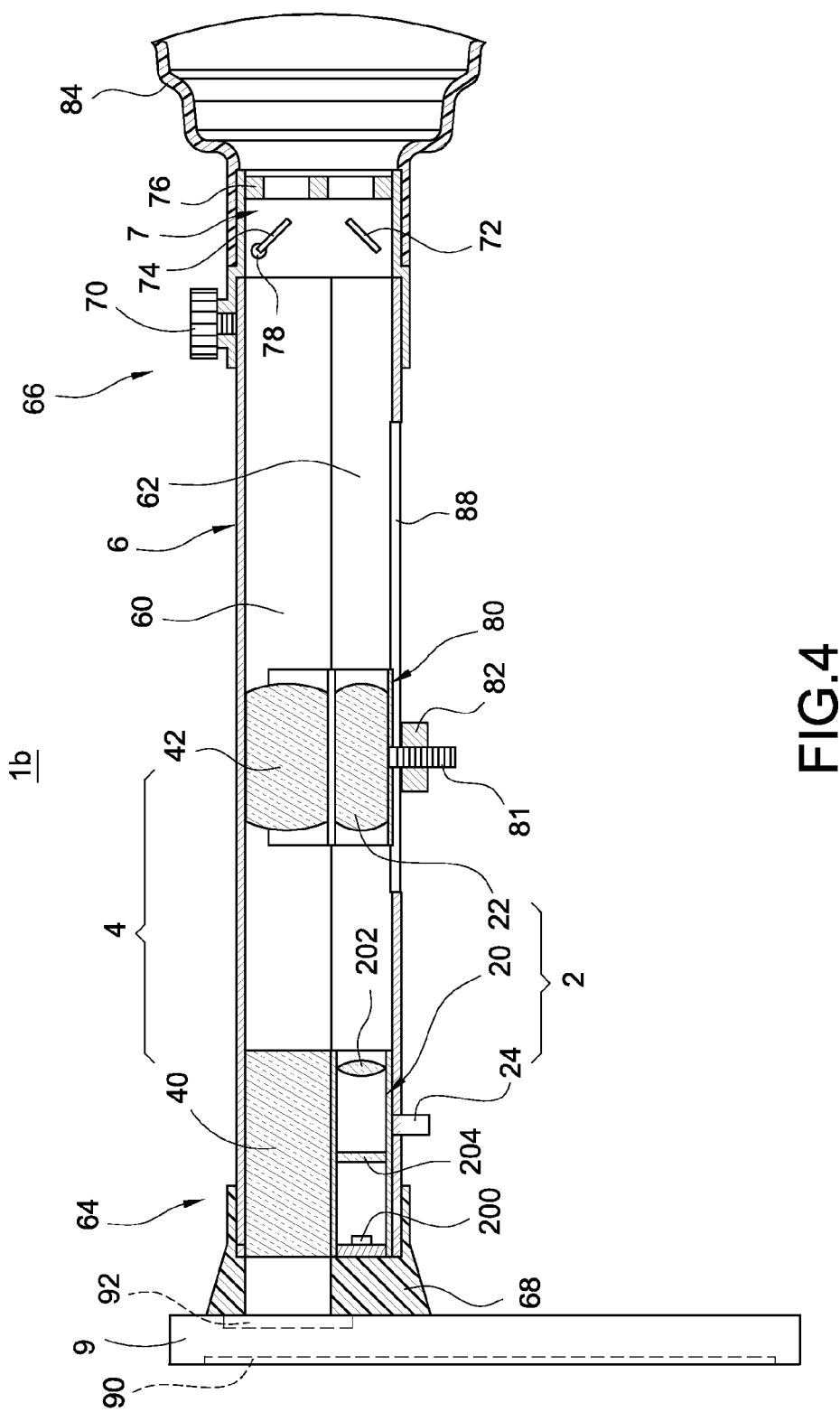
FIG. 4 is a sectional view of the optical system according to the third embodiment of the present invention.

Referred is made to FIG. 3 and FIG. 4, which are a perspective view and a sectional view of an optical system according to a third embodiment of the present invention. The optical system 1b generates a measuring light with uniform intensity for projecting an observed object and transmits an imaging light that has been generated thereof and reflected by the observed object O to a display. The observed object O is, for example, an eyeball. The display is, for example, a screen 90 of a mobile component 9, a complementary metal-oxide-semiconductor (CMOS) or a charge-coupled device (CCD).

The optical system 1b includes an optical apparatus, and the optical apparatus includes an illuminant component 2, an imaging component 4, a fastening component 6, and an optical component 7. The fastening component 6 includes a first through-hole 60 for fastening the imaging component 4 and a second through-hole 62 for fastening the illuminant component 2. The fastening component 6 has a first end 64 and a second end 66 opposite to the first end 64. In this embodiment, the profile of the fastening component 6 is of circular cylinder. However, in the practical use, the observed object O is placed on the second end 62 of the optical system 1b, and inspector inspects the observed object O at the first end 64 of the optical system 1b.

The optical system 1b generates the measuring light to illuminant the observed object O placed on the second end 66, and transmits the imaging light that has been generated from the optical system 1b and reflected by the observed object O to the first end 64, such that the observed object O can be inspect by the inspector. The inspector can inspect the observed object O by a display. And when the display is the screen 90 of the mobile component 9, the optical system 1b may further include a connecting component 68. The connecting component 68 is in contact with the first end 64 of the fastening component 6 for connecting to optical system 1b and the mobile component 9.

The connecting component 68 includes an aperture 680 communicating with the first through-hole 60 while the connecting component 68 is in contact with the first end 64. Another side of the connecting component 68 opposite to the fastening component 6 is in contact with the mobile component 9, and the aperture 680 communicates with a lens 92 of the mobile component 9. Therefore the lens 92 can receive the observed image with imaging light and transmits the observed image with imaging light to the screen 90, and inspector can inspect the observed object O via the screen 90.

The first through-hole 60 and the second through-hole 62 are extend from the first end 64 to the second end 66, in the other words, the first through-hole 60 is parallel to the second through-hole 62, and an aperture of the first through-hole 60 is larger than that of the second through-hole 62. The first through-hole 60 can communicate with the second through-hole 62, or the first through-hole 60 cannot communicate with the second through-hole 62 to increase well optical isolation therebetween. If the measuring light has well collimating (which means the divergent angle of the measuring light is extreme small), the first through-hole 60 can communicate with the second through-hole 62 for convenience manufacture. The fastening component 6 may further include an opening 88 communicating with the second through-hole 62.

The illuminant component 2 is arranged within the second through-hole 62 and includes a lighting module 20 and the lighting lens assembly 22. The lighting module 20 generates a measuring light with uniform intensity and a predetermined pattern.

The light module 20 is arranged at the first end 64 and includes a light emitter 200, a converging lens assembly 202, and a light pattern conditioner 204. The light pattern conditioner 204 is arranged between the light emitter 200 and the converging lens assembly 202. The light emitter 200 emits the measuring light. The light emitter 200 is, for example, a light emitting diode (LED), which has advantages of compact, high intensity and well convergence. The measuring light emitted from the light emitter 200 can be visible light or invisible light.

The light pattern conditioner 204 is arranged in front of the light emitter for modifying light amount of the measuring light that has been emitted from the light emitter 200 and passing therethrough to form the particular pattern. The light pattern conditioner 204 is, for example, an aperture stop and a light shade with a slit. The pattern of the measuring light passing through the light pattern conditioner 204 can be linear, cross-shaped, or circular. Besides, the light pattern conditioner 204 may also limit the size of light point projected to the observed object O so that the measuring light passing therethrough has uniform intensity.

The converging lens assembly 202 converges the measuring light that has been emitted from the light emitter 200 and passing through the light pattern conditioner 204 on the lighting lens assembly 22. The converging lens assembly 202 includes one or more convex lenses, however, the converging lens assembly 202 may also include concave lenses.

The illuminant component 2 further includes a switching component 24 arranged on the fastening component 6 and electrically connected to the light emitter 200. The switching component 24 may locate on the first end 64 of the fastening component 6. The switching component 24 is configured to switch operating statuses of the light emitter 200 so that the light emitter 200 goes on or off. In additions, the switching component 24 also controls the light intensity of the light emitter 200.

The imaging component 4 is arranged within the first through-hole 60 and includes an ocular assembly 40 and an objective assembly 42. The ocular assembly 40 is placed on the first end 64. The objective assembly 42 and the ocular assembly 40 collectively modify magnification of the observed image with imaging light.

The optical component 7 includes a supporting component 70, a mirror 72, and a beam splitter 74. The supporting component 70 is connected to the second end 66 and the fastening component 6 for orientating the mirror 72 and the beam splitter 74. The mirror 72 is located between the illuminant component 2 and the observed object O and corresponding to the second through-hole 62. The beam splitter 74 is located between the mirror 72, the observed object O, and the imaging component 4 and corresponding to the first through-hole 60. Thereby the light emitter 200, the light pattern conditioner 294, the converging lens assembly 72 align in a first axis A1, and the light splitter 74, the objective assembly 42, and the ocular assembly 40 align in a second axis A2, the second axis A2 is parallel to the first axis A1. The mirror 72 reflects the measuring light passing through the lighting lens assembly 22 to the beam splitter 74. The beam splitter 74 reflects the measuring light reflected from the mirror 72 to the observed object O and passes the imaging light that has been generated from the illuminant component 2 and reflected by the observed object O therethrough, so that the observed image with imaging light can be transmitted to the objective assembly 42 and the ocular assembly 40 sequentially, and then the observed image with imaging light reaches the screen 90. Accordingly, the measuring light and the imaging light intersect at the beam splitter 74.

The optical component 7 further includes a plurality of indicators 76 and an adjusting component 78. The indicators 76 are arranged on the supporting component 70 and opposite to the second end 66 of the fastening component 6, namely the indicators 76 face the observed object O. The indicators 76 can be, for example, light generators or spots to lead observed object O to look thereon if the observed object O is eyeball of creature. When the optical system 1b is applied to inspect eyeball, the optical system 1b is dispose near eyeball, and the indicators 76 lead eyeball to look certain direction so that appropriate objective image can be inspected by the inspector. The adjusting component 78 is connected to the beam splitter 64 to control arrangement angle of the beam splitter 74 so that the imaging light and the measuring light can be intersect thereat. In the other words, the adjusting component 78 controls the transmission angles of the measuring light and the imaging light, thereby be measuring light can be transmitted to the observed object O, and the observed image with imaging light can the transmitted to the screen 90.

Besides, the optical system 1b also includes a synchronal-movable mount 80. The synchronal-movable mount 80 holds the lighting lens assembly 22 and the objective assembly 42, and includes a supporting portion 81 penetrating the opening 88 for move the lighting lens assembly 22 and the objective assembly 42 backward and forward between the first end 64 and the second end 66 and within the second through-hole 60 and the first through-hole 62. Thereby the distance between the ocular assembly 42 and objective assembly 42 is changed and then achieves magnification of objective image. In the same time, the size of light point projected to the observed object O is also changed to provide well inspecting effect.

The optical system 1b further includes a fixing component 82 movably assemble with the supporting portion 81. When the synchronal-movable mount 80 is moved to an appropriate position, the fixing component 82 and the fastening component 6 collectively fix the synchronal-movable mount 80 on the position. Besides, the optical system 1b also includes a contacting component 84 connected to the optical component 7 and opposite to the fastening component 6 to face the observed object O, thereby unwell feeling of observed object O when inspection can be reduced.

The first through-hole 60 and the second through-hole 62 formed on the fastening component 6 of the optical system 1b according to the present invention are parallel, and the imaging component 4 and the illuminant component 2 are respectively arranged within the first through-hole 60 and the second through-hole 62, thereby the volume of the optical system 1b can be reduced and then easily to carry. Besides, the optical system 1b uses LED to emit the measuring light so that the volume can be further reduced.

Figure 5:
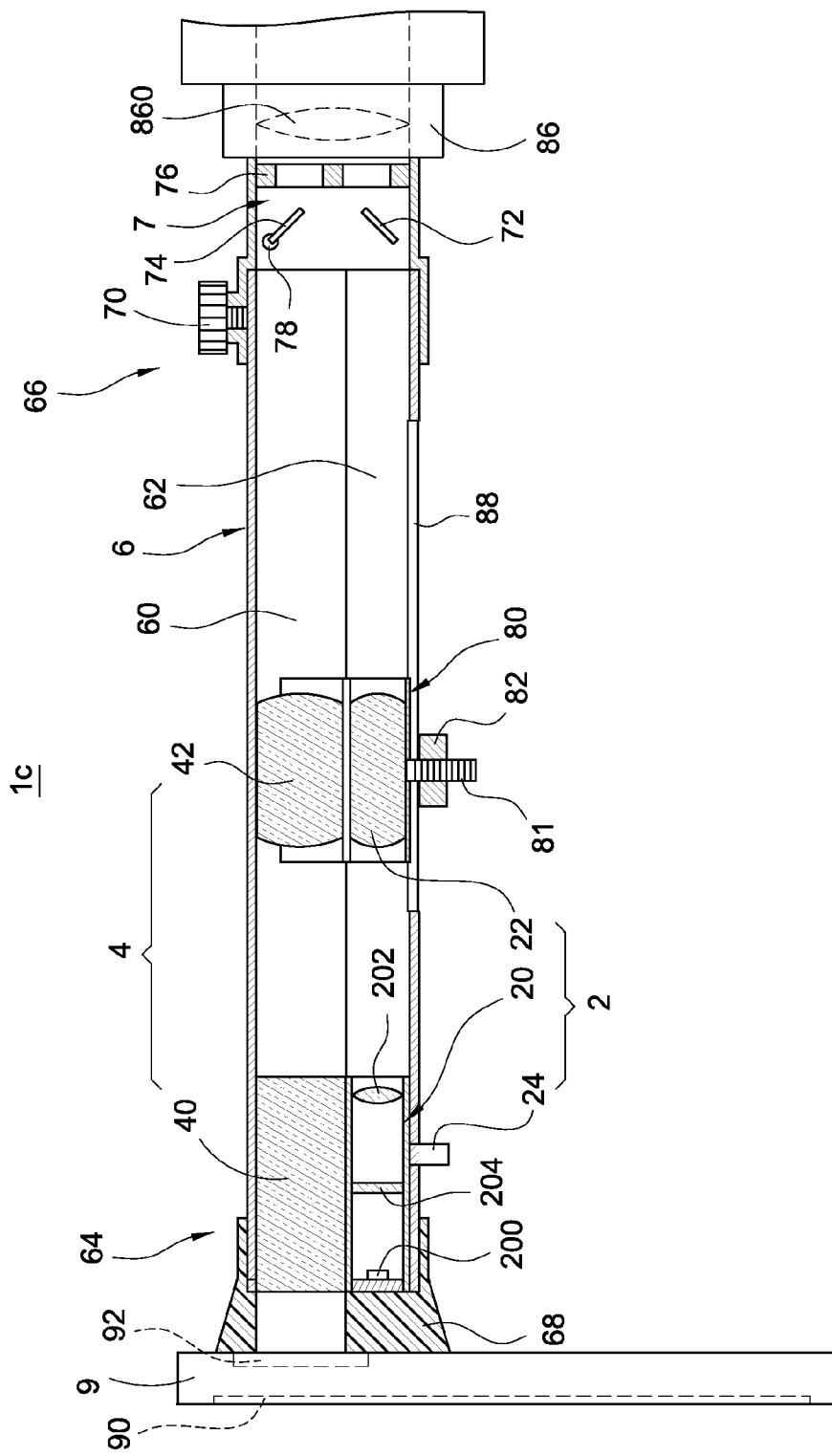
FIG. 5 is a sectional view of an optical system according to a forth embodiment of the present invention.

Furthermore, a microscopy module 86 can be replaced the contacting component 84 to further increase magnification of objective image which is previously limited by the ocular assembly 40 and objective assembly 42, as the optical system 1c shown in FIG. 5. The microscopy module 86 includes a plurality of lenses 860 and achieves magnification with the ocular assembly 40 and the objective assembly 42 in cooperation, and then objective images of eye ground or retina can be inspected.

In measurement, the contacting component 84 stabilizes the optical system 1b. Assuming the observed object O is eyeball, some conditions of acute and superficial ocular diseases such as conjunctivitis, subconjunctival hemorrhage, corneal abrasion, corneal ulcer can be evaluate using the objective images received by the optical system 1b. Besides, in eye ground inspection, a microscopy module 86 is connected to the optical component 7 to magnify objective image of eye ground. Furthermore, the optical system 1b is also used to measure intraocular pressure.

In measurements of surface curvature and intraocular pressure, the illuminant component 2 projects a measuring light to the observed object O (herein the observed object O is eyeball). The measuring light has a predetermined pattern, and in this embodiment, the measuring light is linear. In the practical applications, the measuring light can be cross-shaped or circular. An imaging light that has been generated from the illuminant component 2 and reflected by the observed object is projected to the display 120 via the imaging component 4.

Figure 6:
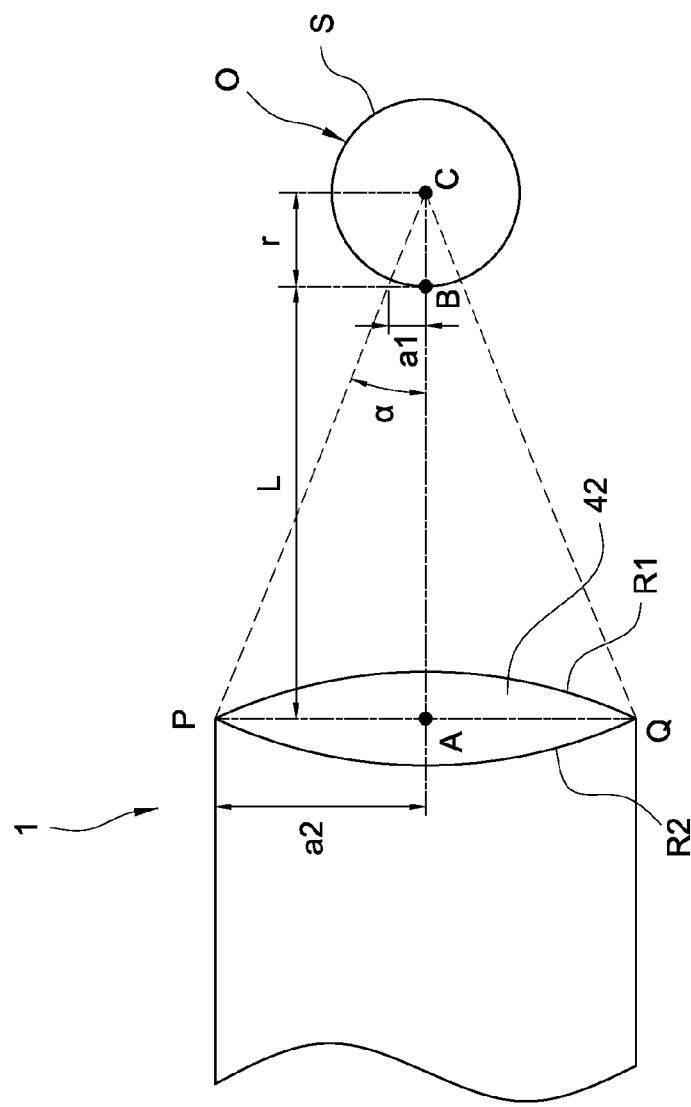
FIG. 6 is a partially sectional view of the optical system according to the first embodiment of the present invention.

Referred is made to FIG. 6. Due to surface curvature of eyeball O is different from person to person, when a measuring light is projected to the eyeball O, an image shown on the display 120 is also different. Therefore a surface curvature of eyeball O can be converted into the image shown on the display 120. For convenience, the beam splitter 74 shown in FIG. 1 is not shown in FIG. 6, however the beam splitter 74 is actually existed between the observed object O and the objective assembly 74.

The measurement of a surface curvature of eyeball O includes steps describe as following:

(a) a measuring light is projected to the eyeball O by the optical system 1.

(b) an imaging light that has generated from the illuminant component 2 and reflected by the observed object O is received by the optical system 1.

(c) a first distance L between a surface S of the eyeball O and a optical center A of the objective assembly 42 of the optical system 1 is measured.

(d) a second distance a2 between a center C of the eyeball O and a rim of the objective assembly 42 is measured. The rim of the objective assembly 42 herein is defined at the position farthest from an optical axis thereof, as points P and Q shown in FIG. 6. The optical axis of the objective assembly 42 is an imaging line passing through the center of curvature of each surface R1 and R2 shown in FIG. 6. In this embodiment, the optical axis of the objective assembly 42 is coincided the extending line of the center C of the eyeball O.

(e) a third distance a1 between an edge of the imaging light and the extending line center C on a tangent of the surface S is measured, where a tangent point B is located on the extending line of the center C. In spatial, the imaging light transmitted from the observed object O to the objective assembly 42 is spread into a solid angle. In a tangent plane perpendicular to the eyeball O and the objective assembly 42, as shown in FIG. 6, the transmitting range of the imaging light is equal to the range formed by the points P, Q, and C, and herein the edge of the imaging light is defined by line PC or QC.

(f) a ratio of the third distance a1 to the second distance a2 is calculated.

(g) a radius of the eyeball O is calculated by formula that r/(L+0=a1/a2, namely a ratio of the radius to a sun of the first distance L and the radius r is equal to the ratio of the third distance a1 to the second distance a2.

(h) an angle α included between the center C and an edge of the imaging light is calculated by formula that tan α=a1/r, namely the angle α has arctangent equal to a ratio of the third distance a1 to the radius r.

(i) a first surface curvature K is calculated by formula that K=a1/α, namely the first surface curvature K is inverse to a ratio of the angle α to the third distance a1. The first surface curvature K means the bending degree of the surface S, and each value of the first surface curvature K corresponds to a particular intraocular pressure.

In order to increase accuracy of measuring intraocular pressure, two surface curvatures (a first surface curvature and a second surface curvature) can be measured in period, and then an intraocular pressure can be converted by a difference between the first surface curvature and the second surface curvature.

Although the present invention has been described with reference to the foregoing preferred embodiment, it will be understood that the invention is not limited to the details thereof. Various equivalent variations and modifications can still occur to those skilled in this art in view of the teachings of the present invention. Thus, all such variations and equivalent modifications are also embraced within the scope of the invention as defined in the appended claims.

What is claimed is:

1. An optical system for measuring an observed object comprising:
    an optical apparatus comprising:
        an illuminant component for generating a measuring light;
        an imaging component comprising an ocular assembly and an objective assembly; and
        an optical component located between the illuminant component and the imaging component, the optical component comprising a mirror and a beam splitter,
    wherein the mirror and the illuminant component are aligned in a first axis; the observed object, the beam splitter, and the objective assembly are aligned in a second axis;
    wherein the beam splitter is disposed between the observed object and the objective assembly;
    wherein the measuring light is reflected to the observed object via the mirror and the beam splitter, an imaging light that has been generated from the illuminant component and reflected by the observed object is projected to the imaging component via the beam splitter, the imaging light and the measuring light intersect at the beam splitter.

2. The optical system in claim 1, wherein the illuminant component comprises:
    a lighting module comprising:
        a light emitter for emitting the measuring light; and
        a light pattern conditioner receiving the measuring light emitted from the light emitter and optically modified the measuring light to have a predetermined pattern; and
    a lighting lens assembly converging the measuring light passing through the light pattern conditioner on the mirror.

3. The optical system in claim 2, wherein the light emitted is a light emitting diode.

4. The optical system in claim 2, wherein the objective assembly is adjacent to the beam splitter, and the ocular assembly is far away from the beam splitter.

5. The optical system in claim 4, wherein the imaging system further comprises a reflecting component arranged between the ocular assembly and the objective assembly, the reflecting component adjusts an optical path of an observed image with imaging light from the objective assembly to project on the ocular assembly.

6. The optical system in claim 4, further comprising:
    a light receiver adjacent to the ocular assembly and configured to receive the observed image with the imaging light and converting the observed image with the imaging light into corresponding electric signal; and
    an electronic component comprising a display configured to receive the electric signal.

7. The optical system in claim 5, further comprising:
    a light receiver adjacent to the ocular assembly and configured to receive the observed image with the imaging light and converting the observed image with the imaging light into corresponding electric signal; and
    an electronic component comprising a display configured to receive the electric signal.

8. The optical system in claim 4, further comprising a fastening component, the fastening component comprising a first end, a second end opposite to the first end, a first through-hole, a second through-hole, and an opening, the first through-hole is parallel to the second through-hole, the first through-hole and the second through-hole respectively extends from the first end to the second end, the opening communicates with the second through-hole, the illuminant component is arranged within the second through-hole, the lighting module is placed on the first end, the imaging component is arranged within the first through-hole and the ocular assembly is placed on the first end, the optical component is connected to the second end, the mirror corresponds to the second through-hole, and the beam splitter corresponds to the first through-hole.

9. The optical system in claim 8, further comprising a synchronal-movable mount holding the lighting lens assembly and the objective assembly, the synchronal-movable mount make the lighting lens assembly and the objective assembly move backward and forward within the second through-hole and the first through-hole.

10. The optical system in claim 1, wherein the optical component further comprises a plurality of indicators arranged at one side of the beam splitter and the mirror and opposite to the imaging component.

11. The optical system in claim 1, further comprising a contacting component connected to the optical component and opposite to the imaging component.

12. The optical system in claim 1, further comprising another optical apparatus, an included angle is formed between the optical apparatuses for generating a stereoscopic image.

13. The optical system, in claim 11, further comprises:
two light receiver corresponding to the ocular assemblies of the imaging components of the optical apparatuses, the light receiver configured to receive imaging lights been generated from the illuminant components and reflected by the observed object, and converting the observed image with image lights into corresponding electric signals; and
an electronic component comprising a display configured to receive the electric signals.

14. The optical system in claim 1, wherein the optical component further comprises an adjusting component connected to the beam splitter.

15. A measurement method applied to the optical system in claim 5, the measurement method used for measuring an eyeball, the measurement method comprising:
(a) projecting a measuring light to the eyeball;
(b) receiving an imaging light reflected by the eyeball;
(c) measuring a first distance between a surface of the eyeball and the optical system;
(d) measuring a second distance between an extending line of a center of the eyeball and a rim of the objective assembly;
(e) measuring a third distance between an edge of the imaging light and the center;
(f) calculating a ratio of the third distance to the second distance;
(g) calculating a radius of the eyeball, wherein a ratio of the radius to a sum of the radius and the first distance is equal to the ratio of the third distance to the second distance;
(h) calculating an angle included between the center to the edge of the imaging light, wherein the angle has arctangent equal to a ratio of the third distance to the radius; and
(i) calculating a first surface curvature of the surface, wherein the first surface curvature is inverse to a ratio of the angle to the third distance.

16. The measuring method in claim 15, further comprising:
(j) repeating step (a) to (i), and obtaining a second surface curvature; and
(k) calculating a difference between the first surface curvature and the second surface curvature to obtain a pressure of the eyeball.

* * * * *